(12) United States Patent
Morita et al.

(10) Patent No.: US 6,395,680 B1
(45) Date of Patent: May 28, 2002

(54) COMPOSITION OF AROMATIC CARBOXYLIC ACID COMPOUNDS AND THERMOSENSITIVE RECORDING MATERIAL USING THE SAME

(75) Inventors: Mitsunobu Morita; Kunio Hayakawa, both of Shizuoka; Ikuo Kameoka, Fukui; Xiaonan Yang, Tochigi, all of (JP)

(73) Assignees: Ricoh Company, Ltd., Tokyo; Nicca Chemical Co., Ltd., Fukui-ken, both of (JP)

( * ) Notice: Subject to any disclaimer, the term of this patent is extended or adjusted under 35 U.S.C. 154(b) by 0 days.

(21) Appl. No.: 09/547,493

(22) Filed: Apr. 12, 2000

(30) Foreign Application Priority Data

Apr. 16, 1999 (JP) ............................................. 11-109772
Apr. 16, 1999 (JP) ............................................. 11-109773

(51) Int. Cl.$^7$ ................................................ B41M 5/20
(52) U.S. Cl. ..................... 503/216; 106/31.17; 503/225
(58) Field of Search ....................... 106/31.17; 503/216, 503/225

(56) References Cited

U.S. PATENT DOCUMENTS

| | | | |
|---|---|---|---|
| 5,306,687 A | 4/1994 | Furuya et al. | 503/207 |
| 5,447,900 A | 9/1995 | Suzaki et al. | 503/207 |
| 5,489,501 A | 2/1996 | Torii et al. | 430/341 |
| 5,827,590 A | 10/1998 | Morita et al. | 428/40.1 |
| 5,919,729 A | 7/1999 | Mori et al. | 503/200 |
| 5,972,836 A | 10/1999 | Morita et al. | 503/207 |

*Primary Examiner*—Bruce H. Hess
(74) *Attorney, Agent, or Firm*—Cooper & Dunham LLP

(57) ABSTRACT

A composition includes at least two aromatic carboxylic acid compounds selected from the group consisting of aromatic carboxylic acid compounds of formulas (I), (II) and (III) as specified in the specification. A thermosensitive recording material has a support, and a thermosensitive coloring layer formed thereon which contains a leuco dye and a color developer capable of inducing color formation in the leuco dye upon application of heat thereto, with the color developer comprising the aforementioned composition of the aromatic carboxylic acid compounds.

8 Claims, No Drawings

COMPOSITION OF AROMATIC CARBOXYLIC ACID COMPOUNDS AND THERMOSENSITIVE RECORDING MATERIAL USING THE SAME

BACKGROUND OF THE INVENTION

1. Field of the Invention

The present invention relates to a composition comprising aromatic carboxylic acid compounds that is capable of effectively serving as a color developer, and a thermosensitive recording material comprising the above-mentioned composition.

2. Discussion of Background

Generally, a thermosensitive recording material comprises a support and a thermosensitive coloring layer formed thereon, which comprises as the main components a colorless or light colored electron-donating dye precursor, and an electron-accepting color developer. These dye precursor and color developer are caused to react instantaneously upon the application of heat thereto to produce recorded images, for instance, using a thermal head, heat pen or laser beam, as disclosed in Japanese Patent Publications 43-4160 and 45-14039.

A thermosensitive recording material is used in a wide variety of fields, for example, as the recording material for an electronic computer, facsimile machine, ticket vending machine, label printer, and recorder because it has the advantages that recording can be achieved using a relatively simple apparatus, maintenance is simple, and there is no noise development.

The above-mentioned thermosensitive recording material employing such an electron-donating dye precursor and an electron-accepting color developer has excellent characteristics such as good appearance and nice touch and is capable of producing images with high coloring density. On the other hand, such a recording material has the disadvantage that the preservation stability of the recorded images is poor. To be more specific, when image areas formed in the thermosensitive recording material come in contact with plastics such as polyvinyl chloride, the image areas are decolorized by the influence of a plasticizer and other additives contained in the plastics. When the colored image areas come in contact with chemicals contained in foods or cosmetics, such image areas are also easily decolorized or the background area easily causes color development.

To improve the preservation stability of the image recorded in the thermosensitive recording material, various color developers with high reliability are conventionally proposed. For instance, the use of a phenolsulfone compound as the color developer is disclosed in Japanese Laid-Open Patent Applications 58-82788 and 60-13852; and the use of a substituted salicylic acid compound, disclosed in Japanese Laid-Open Patent Application 62-169681. However, even though the aforementioned compounds are used as the color developers, the image area formed in the thermosensitive recording material shows still insufficient fastness to plasticizers.

SUMMARY OF THE INVENTION

It is therefore a first object of the present invention to provide a color developer capable of producing colored image areas with improved preservation stability, particularly, in terms of the plasticizer resistance and the oil resistance of the produced image.

A second object of the present invention is to provide a thermosensitive recording material comprising the above-mentioned color developer.

The first object of the present invention can be achieved by a composition comprising at least two aromatic carboxylic acid compounds selected from the group consisting of aromatic carboxylic acid compounds of formulas (I), (II) and (III):

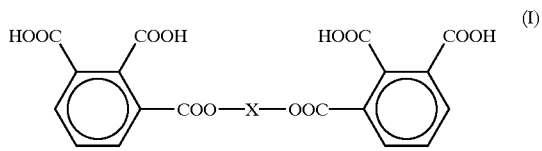

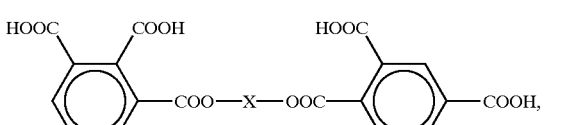

and

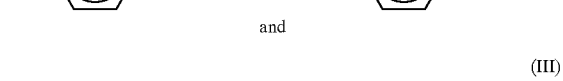

wherein X represents carbonyl group; sulfonyl group; a bivalent group derived from an aliphatic hydrocarbon; a bivalent group derived from an aliphatic hydrocarbon comprising in the main chain thereof at least one hetero atom, carbonyl group, sulfonyl group, an ester linkage, or an aromatic ring; or a bivalent group derived from an aromatic hydrocarbons compound prepared by connecting two aromatic hydrocarbons via at least one hetero atom, carbonyl group, sulfonyl group, an ester linkage, an alkylene, or an aliphatic hydrocarbon comprising a hetero atom in the main chain thereof.

In the formulas (I) to (III), it is preferable that the bivalent functional group represented by X have the following formula (IV):

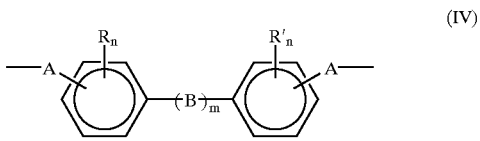

wherein R and R' which may be the same or different are each a hydrogen atom, a halogen atom, an alkyl group having 1 to 8 carbon atoms, an aralkyl group having 1 to 8 carbon atoms, or an aryl group having 1 to 8 carbon atoms; n is an integer of 1 to 4; m is an integer of 0 or 1; and A and B are each carbonyl group, sulfonyl group, a bivalent group derived from an aliphatic hydrocarbon, a bivalent group derived from an aliphatic hydrocarbon comprising in the main chain thereof at least one hetero atom, carbonyl group, sulfonyl group, an ester linkage, or an aromatic ring, or a bivalent group derived from an aromatic hydrocarbon compound prepared by connecting two aromatic hydrocarbons via at least one hetero atom, carbonyl group, sulfonyl group, an ester linkage, an alkylene, or an aliphatic hydrocarbon comprising a hetero atom in the main chain thereof.

Furthermore, it is preferable that the bivalent functional group represented by B in formula (IV) be sulfonyl group.

In addition, it is preferable that the bivalent functional group represented by X in formulas (I) to (III) be derived from a bivalent group selected from the group consisting of an alkylene, oxyalkylene, thioalkylene, sulfinylalkylene, and sulfonylalkylene, each having 1 to 16 carbon atoms.

The above-mentioned second object of the present invention can be achieved by a thermosensitive recording material comprising a support and a thermosensitive coloring layer formed thereon comprising a leuco dye and a color developer capable of inducing color formation in the leuco dye upon application of heat thereto, with the color developer comprising a composition comprising at least two aromatic carboxylic acid compounds selected from the group consisting of aromatic carboxylic acid compounds of the previously mentioned formulas (I), (II) and (III).

DESCRIPTION OF THE PREFERRED EMBODIMENTS

The composition according to the present invention comprises at least two aromatic carboxylic acid compounds selected from the group consisting of aromatic carboxylic acid compounds represented by the aforementioned formulas (I), (II) and (III).

The reasons why the above-mentioned composition of the aromatic carboxylic acid compounds can impart high plasticizer resistance and oil resistance to the colored images formed in the thermosensitive recording material have not yet been clarified, but are considered to be as follows:

(1) The composition of the present invention is provided with excellent color developing capability because the aromatic carboxylic acid compound of formula (I), (II) or (III) contained in the composition is a strong acid having an electron attractive group as the substituent.

(2) The solubility of the aforementioned composition in nonvolatile solvents such as oils and plasticizers can be lowered. This is because the molecular weight of each aromatic carboxylic acid compound is increased by including two or more aromatic carboxylic acids in the molecule thereof.

The composition comprising at least two aromatic carboxylic acid compounds according to the present invention is novel. This composition can be obtained by esterification reaction between a trimellitic acid anhydride and an alcohol compound, for example, in accordance with the following reaction scheme:

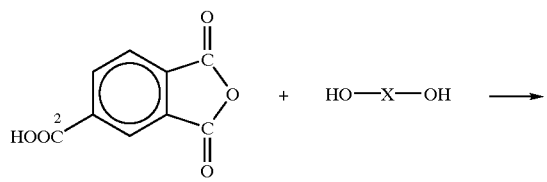

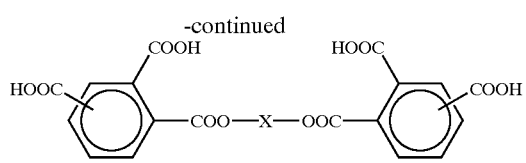

More specifically, the composition of the present invention is obtained in the form of a mixture of at least two aromatic carboxylic acid compounds with carboxyl groups being substituted at different positions, that is, isomers, through the above-mentioned reaction. Namely, there can be obtained a composition comprising the aromatic carboxylic acid compounds of formulas (I) and (II); a composition comprising the aromatic carboxylic acid compounds of formulas (II) and (III); a composition comprising the aromatic carboxylic acid compounds of formulas (I) and (III); and a composition comprising the aromatic carboxylic acid compounds of formulas (I), (II) and (III). Any of the above-mentioned compositions can be used as the color developer for use in the thermosensitive recording material. When necessary, the composition may be separated into the above-mentioned isomers, for example, by recrystallization or chromatography.

Specific examples of the bivalent functional group represented by X in the formulas (I), (II) and (III) include an alkylene, oxyalkylene, bisoxyalkylene, trisoxyalkylene, oxoalkylene, bisoxoalkylene, trisoxoalkylene, thioalkylene, bisthioalkylene, tristhioalkylene, sulfinylalkylene, bissulfinylalkylene, trissulfinylalkylene, sulfonylalkylene, bissulfonylalkylene, trissulfonylalkylene, hydroxyalkylene, bishydroxyalkylene, trishydroxyalkylene, sulfonyldioxyalkylene, bissulfonyldioxyalkylene, trissulfonyldioxyalkylene, carbonyldioxyalkylene, biscarbonyldioxyalkylene, triscarbonyldioxyalkylene, carbamoylalkylene, biscarbamoylalkylene, and triscarbamoylalkylene, each having 1 to 16 carbon atoms.

Further, examples of the bivalent functional group represented by X in the formulas (I), (II) and (III) are as follows:

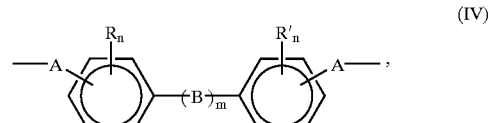 (IV)

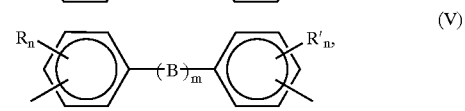 (V)

 (VI)

and

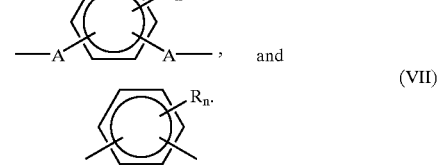 (VII)

In the formulas (IV) to (VII), R and R' which may be the same or different are each a hydrogen atom, a halogen atom, an alkyl group having 1 to 8 carbon atoms, an aralkyl group having 1 to 8 carbon atoms, or an aryl group having 1 to 8 carbon atoms; and n is an integer of 1 to 4.

Specific examples of the bivalent group represented by A in the above-mentioned formulas (IV) and (VI) include an alkylene, oxyalkylene, bisoxyalkylene, trisoxyalkylene, oxoalkylene, bisoxoalkylene, trisoxoalkylene, thioalkylene, bisthioalkylene, tristhioalkylene, sulfinylalkylene, bissulfinylalkylene, trissulfinylalkylene, sulfonylalkylene, bissulfonylalkylene, trissulfonylalkylene, hydroxyalkylene, bishydroxyalkylene, trishydroxyalkylene, sulfonyldioxyalkylene, bissulfonyldioxyalkylene, trissulfonyldioxyalkylene, carbonyldioxyalkylene, biscarbonyldioxyalkylene, triscarbonyldioxyalkylene, carbamoylalkylene, biscarbamoylalkylene, and triscarbamoylalkylene, each having 1 to 16 carbon atoms.

With respect to B in the aforementioned formulas (IV) and (V), m is an integer of 0 or 1. When m is an integer of 1, specific examples of the group represented by B in the aforementioned formulas (IV) and (V) are oxygen atom, carbonyl group, sulfur atom, sulfinyl group, sulfonyl group, sulfonyloxy group, carbonyloxy group, carbonylamino group, urea group, hydrazinocarbonyl group, hydrazinosulfonyl group, phenylene, biphenylene, xylylene,

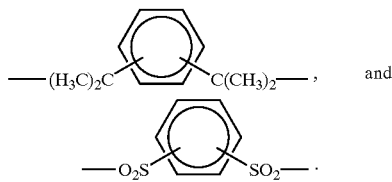

Furthermore, there can be employed as the bivalent group represented by B in the formulas (IV) and (V) an alkylene, oxyalkylene, bisoxyalkylene, trisoxyalkylene, oxoalkylene, bisoxoalkylene, trisoxoalkylene, thioalkylene, bisthioalkylene, tristhioalkylene, sulfinylalkylene, bissulfinylalkylene, trissulfinylalkylene, sulfonylalkylene, bissulfonylalkylene, trissulfonylalkylene, hydroxyalkylene, bishydroxyalkylene, trishydroxyalkylene, sulfonyldioxyalkylene, bissulfonyldioxyalkylene, trissulfonyldioxyalkylene, carbonyldioxyalkylene, biscarbonyldioxyalkylene, triscarbonyldioxyalkylene, carbamoylalkylene, biscarbamoylalkylene, and triscarbamoylalkylene, each having 1 to 16 carbon atoms.

For instance, when the bivalent group X in the formulas (I), (II) and (III) is $-C_2H_4-$, that is represented by the example No. (1) for convenience, there can be obtained a composition comprising at least two aromatic carboxylic acid compounds selected from the group consisting of the following three isomers of formulas (1-I), (1-II), and (1-III):

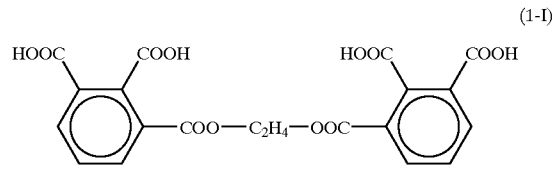

(1-I)

(1-II)

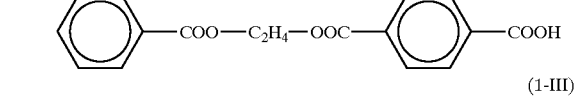

(1-III)

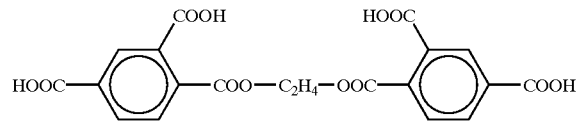

Other examples of the bivalent group X are shown in TABLE 1, and in each case, there can be similarly obtained a composition comprising at least two aromatic carboxylic acid compounds selected from the group consisting of the three isomers as represented by the formulas (1-I) to (1-III).

TABLE 1

| | |
|---|---|
| $-C_3H_6-$ | (2) |
| $-C_4H_8-$ | (3) |
| $-C_5H_{10}-$ | (4) |
| $-C_6H_{12}-$ | (5) |
| $-C_7H_{14}-$ | (6) |
| $-C_{10}H_{20}-$ | (7) |
| $-CH_2\underset{\underset{CH_3}{\vert}}{\overset{\overset{CH_3}{\vert}}{C}}CH_2-$ | (8) |
| $-C_2H_4OC_2H_4-$ | (9) |
| $-C_2H_4(OC_2H_4)_2-$ | (10) |
| $-C_2H_4(OC_2H_4)_3-$ | (11) |
| $-C_2H_4(OC_2H_4)_4-$ | (12) |
| $-C_3H_6OC_3H_6-$ | (13) |
| $-C_3H_6(OC_3H_6)_2-$ | (14) |
| $-CH_2\overset{\overset{O}{\|}}{C}CH_2-$ | (15) |
| $-C_2H_4SC_2H_4-$ | (16) |
| $-C_2H_4SC_2H_4SC_2H_4-$ | (17) |
| $-C_3H_6SC_3H_6-$ | (18) |

TABLE 1-continued

| | |
|---|---|
| $-C_2H_4SSC_2H_4-$ | (19) |
| $-C_2H_4\overset{\overset{O}{\|}}{S}C_2H_4-$ | (20) |
| $-C_2H_4\overset{\overset{O}{\|}}{S}C_2H_4\overset{\overset{O}{\|}}{S}C_2H_4-$ | (21) |
| $-C_3H_6\overset{\overset{O}{\|}}{S}C_3H_6-$ | (22) |
| $-C_2H_4-\overset{\overset{O}{\|}}{S}-\overset{\overset{O}{\|}}{S}-C_2H_4-$ | (23) |
| $-C_2H_4\overset{\overset{O}{\|}}{\underset{\underset{O}{\|}}{S}}C_2H_4-$ | (24) |
| $-C_2H_4\overset{\overset{O}{\|}}{\underset{\underset{O}{\|}}{S}}C_2H_4\overset{\overset{O}{\|}}{\underset{\underset{O}{\|}}{S}}CH_4-$ | (25) |
| $-C_3H_6\overset{\overset{O}{\|}}{\underset{\underset{O}{\|}}{S}}C_3H_5-$ | (26) |
| $-C_2H_4-\overset{\overset{O}{\|}}{\underset{\underset{O}{\|}}{S}}-\overset{\overset{O}{\|}}{\underset{\underset{O}{\|}}{S}}-C_2H_4-$ | (27) |
| $-CH_2\overset{\overset{OH}{\|}}{C}HCH_2-$ | (28) |
| $-C_2H_4\overset{\overset{OH}{\|}}{C}HCH_2-$ | (29) |
| $-C_2H_4O-\langle\bigcirc\rangle-\langle\bigcirc\rangle-OC_2H_4-$ | (30) |
| $-C_2H_4O-\langle\bigcirc\rangle-CH_2-\langle\bigcirc\rangle-OC_2H_4-$ | (31) |
| $-C_2H_4O-\langle\bigcirc\rangle-\underset{\underset{CH_3}{\|}}{\overset{\overset{CH_3}{\|}}{C}}-\langle\bigcirc\rangle-OC_2H_4-$ | (32) |
| $-C_2H_4O-\langle\bigcirc(CH_3)\rangle-\underset{\underset{CH_3}{\|}}{\overset{\overset{CH_3}{\|}}{C}}-\langle\bigcirc(CH_3)\rangle-OC_2H_4-$ | (33) |

TABLE 1-continued

(34) —C₂H₄O—[3,5-dimethyl-4-...]—C(CH₃)₂—[3,5-dimethyl-phenyl]—OC₂H₄—

(35) —C₂H₄O—[3,5-dibromo-phenyl]—C(CH₃)₂—[3,5-dibromo-phenyl]—OC₂H₄—

(36) —C₂H₄O—[phenyl]—C(CH₃)₂—[phenyl]—C(CH₃)₂—[phenyl]—OC₂H₄—

(37) —C₂H₄O—[phenyl]—OCH₂CH₂O—[phenyl]—OC₂H₄—

(38) —C₂H₄O—[phenyl]—SO₂—[phenyl]—OC₂H₄—

(39) —C₂H₄O—[phenyl]—SO₂—[phenyl]—OC₂H₄—

(40) —C₂H₄O—[3-methyl-phenyl]—SO₂—[3-methyl-phenyl]—OC₂H₄—

(41) —C₂H₄O—[3,5-dimethyl-phenyl]—SO₂—[3,5-dimethyl-phenyl]—OC₂H₄—

(42) —C₂H₄O—[3,5-dibromo-phenyl]—SO₂—[3,5-dibromo-phenyl]—OC₂H₄—

(43) —C₂H₄O—[phenyl]—SO₂C₃H₈SO₂—[phenyl]—OC₂H₄—

(44) —C₂H₄O—[phenyl]—SO₂C₂H₄SO₂C₂H₄SO₂—[phenyl]—OC₂H₄—

TABLE 1-continued
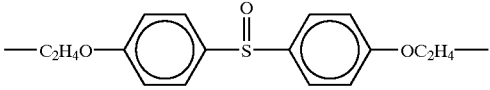 (45)
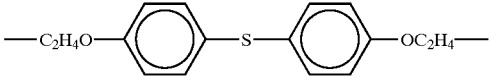 (46)
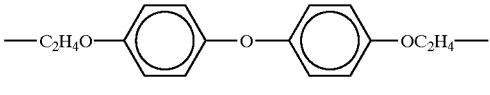 (47)
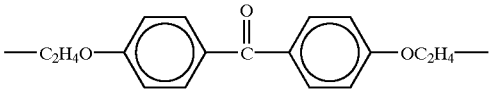 (48)
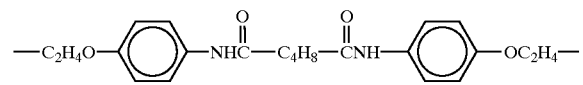 (49)
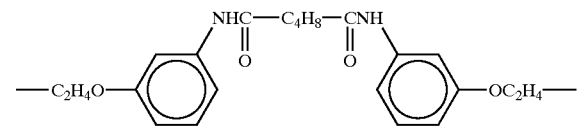 (50)
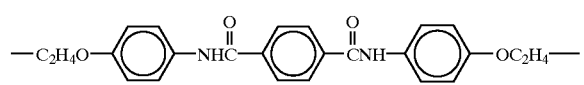 (51)
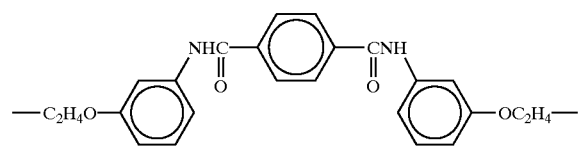 (52)
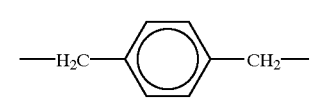 (53)
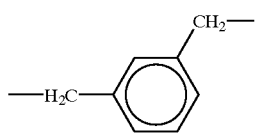 (54)
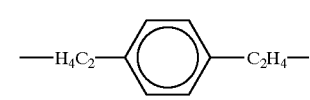 (55)
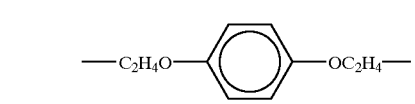 (56)
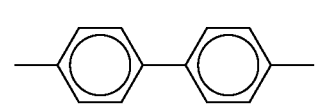 (57)
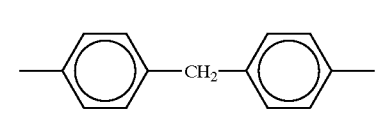 (58)

TABLE 1-continued
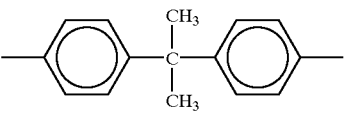 (59)
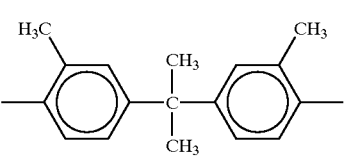 (60)
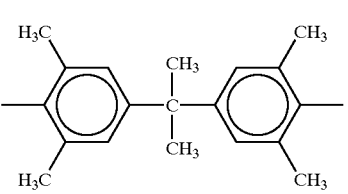 (61)
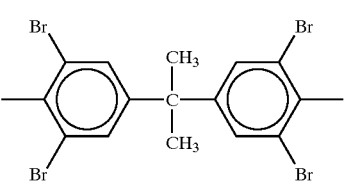 (62)
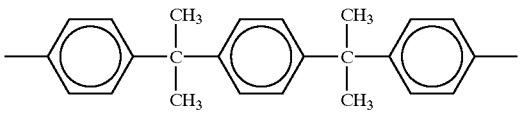 (63)
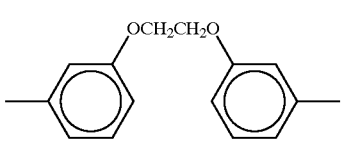 (64)
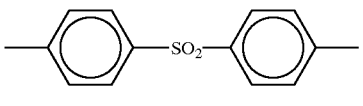 (65)
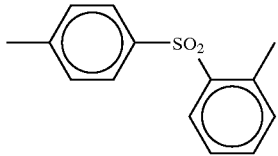 (66)
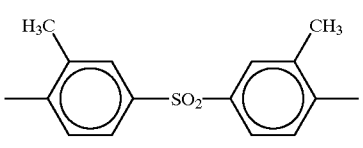 (67)
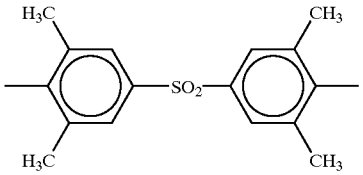 (68)

TABLE 1-continued
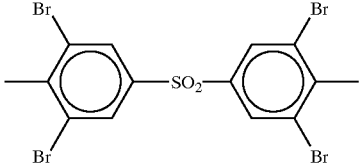 (69)
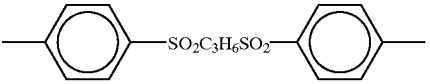 (70)
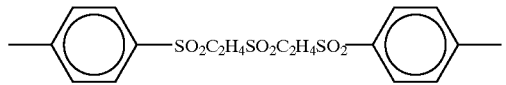 (71)
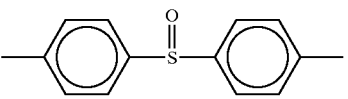 (72)
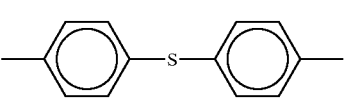 (73)
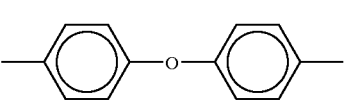 (74)
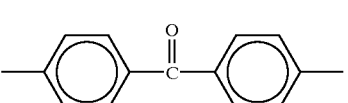 (75)
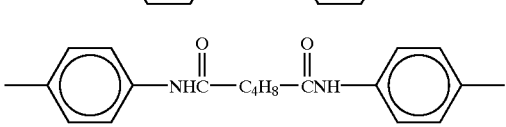 (76)
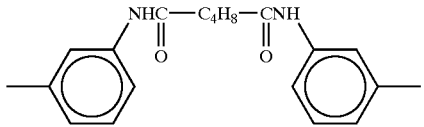 (77)
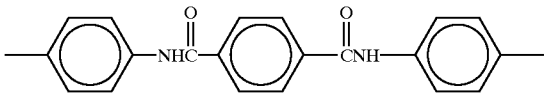 (78)
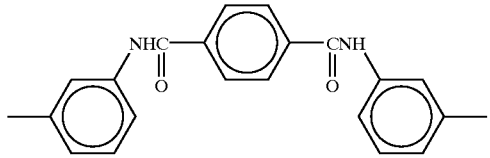 (79)
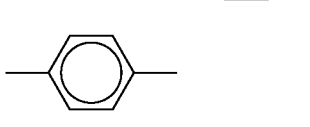 (80)
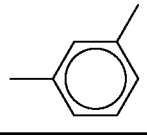 (81)

When the above-mentioned composition of aromatic carboxylic acid compounds represented by formulas (I) to (III) is contained in the thermosensitive coloring layer, it is preferable that the amount of the composition be in the range of 1 to 10 g/m$^2$, more preferably in the range of 1 to 5 g/m$^2$ on a dry basis.

The above-mentioned basic dye precursors such as leuco dyes can be used alone or in combination together with the color developer in the thermosensitive coloring layer. Any leuco dyes that are conventionally employed in the thermosensitive recording material are usable in the present invention.

Specific examples of the leuco dyes are as follows:
3,3-bis(p-dimethylaminophenyl)phthalide,
3,3-bis(p-dimethylaminophenyl)-6-dimethylaminophthalide,
3-diethylamino-6-methyl-7-anilinofluoran,
3-dibutylamino-6-methyl-7-anilinofluoran,
3-N-methyl-N-butylamino-6-methyl-7-anilinofluoran,
3-N-methyl-N-propylamino-6-methyl-7-anilinofluoran,
3-N-ethyl-N-propylamino-6-methyl-7-anilinofluoran,
3-N-methyl-N-amylamino-6-methyl-7-anilinofluoran,
3-N-ethyl-N-amylamino-6-methyl-7-anilinofluoran,
3-N-ethyl-N-isoamylamino-6-methyl-7-anilinofluoran,
3-N-hexyl-N-isoamylamino-6-methyl-7-anilinofluoran,
3-N-methyl-N-cyclohexylamino-6-methyl-7-anilinofluoran,
3-N-ethyl-N-furanylmethylamino-6-methyl-7-anilinofluoran,
3-diethyl-N-butylamino-7-(2'-fluoroanilino)fluoran,
3-pyrrolidyl-7-dibenzylaminofluoran,
3-bis(diphenylamino)fluoran,
3-diethylamino-7-(2'-chloroanilino)fluoran,
3-diethylamino-6-chloro-7-anilinofluoran,
3-dibutylamino-7-(2'-chloroanilino)fluoran,
3-diethylamino-7-chlorofluoran,
3-diethylamino-6-methyl-7-chlorofluoran,
3-N-methyl-N-cyclohexylamino-6-chlorofluoran,
3-diethylamino-6-methyl-7-(2',4'-dimethylanilino)fluoran,
3-diethylamino-7-dibenzylaminofluoran,
3-butylamino-7-(2'-chloroanilino)fluoran, and
3-diethylamino-6-ethoxyethyl-7-anilinofluoran.

The composition comprising the aromatic carboxylic acid compounds according to the present invention may be used alone as the color developer in the thermosensitive recording material. Alternatively, the aforementioned composition may be used in combination with the conventional color developers. In this case, the composition of the present invention can also serve as, for example, a sensitizer.

Specific examples of the conventional color developers for use in the present invention are as follows:
4,4'-isopropylidenebisphenol,
4,4'-isopropylidenebis(o-methylphenol),
4,4'-sec-butylidenebisphenol,
4,4'-isopropylidenebis(2-tert-butylphenol),
zinc p-nitrobenzoate,
1,3,5-tris(4-tert-butyl-3-hydroxy-2,6-dimethylbenzyl) isocyanuric acid,
2,2-(3,4-dihydroxyphenylpropane),
bis(4-hydroxy-3-methylphenylsulfide),
4-[β-(p-methoxyphenoxy)ethoxy]salicylic acid,
1,7-bis(4-hydroxyphenylthio)-3,5-dioxaheptane,
monobenzyl phthalate monocarboxylic acid,
4,4'-cyclohexylidenebisphenol,
4,4'-isopropylidenebis(2-chlorophenol),
2,2'-methylenebis(4-methyl-6-tert-butylphenol),
4,4'-butylidenebis(6-tert-butyl-2-methyl)phenol,
1,1,3-tris(2-methyl-4-hydroxy-5-cyclohexyl)butane,
4,4'-thiobis(6-tert-butyl-2-methylphenol),
4,4'-diphenolsulfone,
4-benzyloxy-4'-hydroxydiphenylsulfone, 4-isopropyloxy-4'-hydroxydiphenylsulfone,
4,4'-diphenolsulfoxide,
isopropyl p-hydroxybenzoate,
benzyl p-hydroxybenzoate,
benzyl protocatechuate,
stearyl gallate,
1,3-bis(4-hydroxyphenylthio)propane,
1,3-bis(4-hydroxyphenylthio)-2-hydroxypropane,
N,N-diphenylthiourea,
N,N-di(m-chlorophenylthiourea),
salicylanilide,
5-chlorosalicylanilide,
bis(4-hydroxyphenyl)methyl acetate,
bis(4-hydroxyphenyl)benzyl acetate,
1,3-bis(4-hydroxycumyl)benzene,
1,4-bis(4-hydroxycumyl)benzene,
2,4'-diphenolsulfone,
2,2'-diallyl-4,4'-diphenolsulfone,
3,4-dihydroxy-4'-methyldiphenylsulfone,
α,α-bis(4-hydroxyphenyl)-α-methyltoluene,
4,4'-thiobis(2-methylphenol), and
4,4'-thiobis(2-chlorophenol).

According to the present invention, the thermosensitive coloring layer may further comprise a variety of thermofusible materials as a thermosensitivity-improving agent and a lubricant. In such a case, the thermofusible material may be used alone or in combination.

Specific examples of the thermofusible materials are as follows: fatty acids such as stearic acid and behenic acid; fatty amides such as stearamide and palmitamide; fatty acid metallic salts such as zinc stearate, aluminum stearate, calcium stearate, zinc palmitate, and zinc behenate; and p-benzylbiphenyl, terphenyl, triphenylmethane, benzyl p-benzyloxybenzoate, β-benzyloxy naphthalene, phenyl β-naphthoate, phenyl 1-hydroxy-2-naphthoate, methyl 1-hydroxy-2-naphthoate, diphenyl carbonate, benzyl terephthalate, 1,4-dimethoxynaphthalene, 1,4-diethoxynaphthalene, 1,4-dibenzyloxynaphthalene, 1,2-diphenoxyethane, 1,2-bis(4-methylphenoxyethane), 1,4-diphenoxy-2-butene, 1,2-bis(4-methoxyphenylthio)ethane, dibenzoylmethane, 1,4-diphenylthiobutane, 1,4-diphenylthio-2-butene, 1,3-bis(2-vinyloxyethoxy)benzene, 1,4-bis(2-vinyloxyethoxy)benzene, p-(2--vinyloxyethoxy) biphenyl, p-aryloxybiphenyl, dibenzoyloxymethane, dibenzoyloxypropane, dibenzyl disulfide, 1,1-diphenylethanol, 1,1-diphenylpropanol, p-benzyloxybenzyl alcohol, 1,3-phenoxy-2-propanol, N-octadecylcarbamoyl-p-methoxycarbonylbenzene, N-octadecylcarbamoylbenzene, 1,2-bis(4-methoxyphenoxy)propane, 1,5-bis(4-methoxyphenoxy)-3-oxapentane, dibenzyl oxalate, bis(4-methylbenzyl)oxalate, and bis(4-chlorobenzyl)oxalate.

When the thermosensitive recording material of the present invention is prepared, not only the above-mentioned color developer such as the composition of the aromatic carboxylic acid compounds, leuco dye, and thermofusible material, but also other materials for constituting the conventional thermosensitive recording material may be appropriately employed. For instance, a variety of binder agents for binding the materials for constituting the thermosensitive coloring layer to the support may be used. Such binder agents may be used alone or in combination.

Specific examples of the binder agent for use in the thermosensitive coloring layer include water-soluble polymers such as poly(vinyl alcohol), modified poly(vinyl alcohol), starch and starch derivatives, cellulose derivatives such as methoxy cellulose, hydroxyethyl cellulose, carboxymethyl cellulose, methyl cellulose, and ethyl cellulose, sodium polyacrylate, poly(vinylpyrrolidone), acrylamide-acrylic ester copolymer, acrylamide-acrylic ester-methacrylic acid terpolymer, alkali salts of styrene-maleic anhydride copolymer, alkali salts of isobutylene-maleic anhydride copolymer, polyacrylamide, modified polyacrylamide, methyl vinyl ether-maleic anhydride copolymer, carboxy-modified polyethylene, vinyl alcohol-acrylamide block copolymer, melamine-formaldehyde resin, urea-formaldehyde resin, sodium alginate, gelatin, and casein; emulsions such as poly(vinyl acetate), polyurethane, styrene-butadiene copolyer, styrene-butadiene-acrylic copolymer, poly(acrylic acid), polyacrylate, polymethacrylate, vinyl chloride-vinyl acetate copolymer, poly(butyl methacrylate), poly(vinyl butyral), poly(vinyl acetal), and ethylene-vinyl acetate copolymer.

The above-mentioned binder agents may be cured by the addition of a crosslinking agent (curing agent) when necessary. In this case, the crosslinking agent (curing agent) capable of reacting with the binder agents, for example, glyoxal derivatives, methylol derivatives, epichlorohydrin derivatives, epoxy compounds, and aziridine compounds are usable.

Furthermore, the thermosensitive coloring layer may further comprise a pigment.

Examples of the pigment for use in the thermosensitive coloring layer are finely-divided inorganic particles of silica, zinc oxide, titanium oxide, aluminum hydroxide, zinc hydroxide, barium sulfate, clay, kaolin, calcined kaolin, talc, and surface-treated silica; and finely-divided organic particles of urea-formalin resin, styrene-methacrylic acid copolymer, polystyrene resin, vinylidene chloride resin, styrene-acrylic copolymer, and various kinds of plastic spherical minute void particles.

The thermosensitive recording material of the present invention may further comprise a protective layer which is overlaid on the thermosensitive coloring layer in order to improve the head-matching properties, that is, the matching properties of the thermosensitive recording material with a thermal head, enhance the preservation stability of the recorded images, and upgrade the writing and printing quality of the recording material.

The protective layer may comprises a pigment, a binder agent, a crosslinking agent, and a lubricant. The same pigments, binder agents, crosslinking agents, and lubricants (thermofusible material) as previously described are usable for the formation of the protective layer. With respect to each of these materials, such as the pigment or binder agent, one kind of material component may be used alone or two or more kinds of material components may be used in combination.

The thermosensitive recording material of the present invention may further comprise an undercoat layer which is interposed between the support and the thermosensitive coloring layer. The undercoat layer comprising as the main components a pigment and a binder agent can serve as a heat insulating layer. Namely, owing to the presence of the undercoat layer, thermal energy supplied to the thermosensitive recording material by the thermal head can be efficiently utilized, thereby improving the thermal sensitivity of the recording material. With respect to the pigment or binder agent for use in the undercoat layer, the above-mentioned pigment components or binder agent components may be independently used alone or in combination. In particular, it is desirable to use as the pigment plastic spherical void particles in the undercoat layer.

The plastic spherical void particles for use in the present invention comprise a thermoplastic resin for forming a shell of each void particle. Air or other gasses are contained in the void particles in the expanded state.

It is preferable that the average particle diameter (outer diameter) of the void particles be in the range of about 0.2 to 20 $\mu$m. When the average particle size of the void particles is within the aforementioned range, there is no problem in the production because the voidage of the void particles can freely be determined. In addition, the surface smoothness of the undercoat layer obtained by coating is not excessively decreased. Therefore, the adhesion of the surface of the thermosensitive recording material to the thermal head does not lower, and consequently, deterioration of the thermal sensitivity of the recording material can be avoided. Further, it is preferable that the void particles classified in a narrow distribution be employed in the undercoat layer.

It is preferable that the voidage of the spherical void particles for use in the undercoat layer be 40% or more, and more preferably 90% or more, from the viewpoint of the heat insulating effect. When the voidage is within the above range, sufficient heat insulating effect of the undercoat layer can be obtained, so that the thermal energy supplied by the thermal head can be inhibited from escaping through the support of the thermosensitive recording material. As a result, the effect of improving the thermal sensitivity does not deteriorate.

In the present invention, the voidage of the plastic spherical void particles for use in the undercoat layer is expressed by the following formula:

$$\text{Voidage } (\%) = \frac{(\text{Inner diameter of void particle})}{(\text{Outer diameter of void particle})} \times 100$$

Specific examples of the thermoplastic resin for forming a shell of the void particle are polystyrene, poly(vinyl chloride), poly(vinylidene chloride), poly(vinyl acetate), poly(acrylic ester), polyacrylonitrile, polybutadiene, and copolymer resins comprising the monomers for use in the above-mentioned resins. Of those thermoplastic resins, a copolymer resin comprising as the main component vinylidene chloride or acrylonitrile is preferably employed in the present invention.

A binder resin for the formation of the above-mentioned undercoat layer may be appropriately selected from the conventional water-soluble polymers and aqueous polymeric emulsions.

Specific examples of the binder agent for use in the undercoat layer are water-soluble polymers such as poly (vinyl alcohol), starch and starch derivatives, cellulose derivatives such as methoxy cellulose, hydroxyethyl cellulose, carboxymethyl cellulose, methyl cellulose and ethyl cellulose, sodium polyacrylate, poly(vinylpyrrolidone), acrylamide—acrylic ester copolymer, acrylamice—acrylic ester—methacrylic acid terpolymer, alkali salts of styrene—maleic anhydride copolymer, alkali salts of isobutylene—maleic anhydrice copolymer, polyacrylamide, sodium aliginate, gelatin, and casein; and aqueous polymeric emulsions including latexes such as styrene—butadiene copolymer and styrene—butadiene—acryl copolymer, and emulsions such as vinyl acetate resin, vinyl acetate—acrylic acid copolymer, styrene—acrylic ester copolymer, acrylic ester resin, and polyurethane resin.

In the undercoat layer for use in the present invention, the previously mentioned plastic spherical void particles and binder resin may be used in combination with auxiliary additive components such as a filler, a thermofusible material, a surface active agent, and an agent for preventing color development by the application of pressure, which are used in the conventional thermosensitive recording materials. Specific examples of the filler and the thermofusible material for use in the undercoat layer are the same as those mentioned in the formation of the thermosensitive coloring layer. Further, when the plastic spherical void particles are contained in the undercoat layer, it is recommendable that an inorganic pigment be contained in the undercoat layer in order to improve the head-matching properties.

Furthermore, in the present invention, an intermediate layer comprising a pigment, a binder agent and a thermofusible material may be interposed between the undercoat layer and the thermosensitive coloring layer when necessary.

The thermosensitive recording material of the present invention may further comprise a backcoat layer which is provided on the back surface of the support, opposite to the thermosensitive coloring layer with respect to the support. The backcoat layer may comprise the same pigment, binder agent, and lubricant (thermofusible material) as mentioned above.

As the support of the thermosensitive recording material, a sheet of plain paper, such as acidic paper and alkaline paper, and other support members on which a coating liquid can be coated may freely be used. For example, a sheet of synthetic paper and a polymeric film are usable as the support.

The thermosensitive recording material of the present invention is applicable in any fields that employ the conventional thermosensitive recording materials. For instance, the thermosensitive recording material can be used as a paper for facsimile machine, a point-of-sales (POS) label for food, a bar code label for industrial applications, a thermosensitive recording adhesive label of liner-less type, a ticket paper, a magnetic ticket paper, a paper for CAD, and a transparent thermosensitive film.

Other features of this invention will become apparent in the course of the following description of exemplary embodiments, which are given for illustration of the invention and are not intended to be limiting thereof.

PREPARATION EXAMPLE 1
[Synthesis of composition No. 38 of aromatic carboxylic acid compounds employing a bivalent group X represented by No. 38 in Table 1]

A mixture of 84.5 g (0.25 mol) of bis[4-(2-hydroxyethoxy) phenyl]sulfone, 114.1 g (0.60 mol) of trimellitic acid anhydride, and 151.5 g (1.50 mol) of triethylamine was suspended in a mixed solvent of 150 g of tetrahydrofuran and 50 g of dimethylformamide in a reaction vessel. The mixture was heated at about 83° C. under reflux to carry out the reaction for 3 hours.

After the reaction mixture was cooled, 100 ml of water was dropwise added to the reaction mixture. The resulting mixture was stirred for about 30 minutes, and dilute hydrochloric acid was dropwise added to the mixture to adjust the mixture to pH 2 or less.

The above-mentioned mixture was separated into two layers on standing. The organic layer was washed with water until a reaction product crystallized. As a result, 163.0 g of white crystals was obtained in a 90% yield. This reaction product was a composition made of three kinds of isomers. The purity of the composition was 95.3% when measured by high performance liquid chromatography (PHLC), and the melting point thereof was 195–212° C. The corresponding reaction product was identified as the expected composition by the analysis of $^1$H-NMR.

δ (ppm)=13.50 (broad s), 8.22 (4H, t), 7.79 (6H, t), 7.17 (4H, d), 4.63 (4H, broad s), 4.44 (4H, broad s).

PREPARATION EXAMPLE 2
[Synthesis of composition No. 40 of aromatic carboxylic acid compounds employing a bivalent group X represented by No. 40 in Table 1]

A mixture of 91.5 g (0.25 mol) of bis[3-methyl-4-(2-hydroxyethoxy)phenyl]sulfone, 114.1 g (0.60 mol) of trimellitic acid anhydride, and 151.5 g (1.50 mol) of triethylamine was suspended in a mixed solvent of 150 g of tetrahydrofuran and 50 g of dimethylformamide in a reaction vessel. The mixture was heated at about 83° C. under reflux to carry out the reaction for 3 hours.

After the reaction mixture was cooled, 100 ml of water was dropwise added to the reaction mixture. The resulting mixture was stirred for about 30 minutes, and dilute hydrochloric acid was dropwise added to the mixture to adjust the mixture to pH 2 or less.

The above-mentioned mixture was separated into two layers on standing. The organic layer was washed with water until a reaction product crystallized. As a result, 178.1 g of white crystals was obtained in a 95% yield. This reaction product was a composition made of three kinds of isomers. The purity of the composition was 96.1% (when measured by the HPLC), and the melting point thereof was 213–232° C. The corresponding reaction product was identified as the expected composition by the analysis of $^1$H-NMR.

δ (ppm)=8.24 (4H, t), 7.85 (2H, d), 7.77 (4H, d), 7.22 (2H, d), 4.70 (4H, t), 4.38 (4H, t), 2.20 (6H, s).

PREPARATION EXAMPLE 3
[Synthesis of composition No. 32 of aromatic carboxylic acid compounds employing a bivalent group X represented by No. 32 in Table 1]

A mixture of 79.1 g (0.25 mol) of 2,2'-bis[4-(2-hydroxyethoxy)phenyl]propane, 114.1 g (0.60 mol) of trimellitic acid anhydride, and 151.5 g (1.50 mol) of triethylamine was suspended in a mixed solvent of 150 g of tetrahydrofuran and 50 g of dimethylformamide in a reaction vessel. The mixture was heated at about 83° C. under reflux to carry out the reaction for 3 hours.

After the reaction mixture was cooled, 100 ml of water was dropwise added to the reaction mixture. The resulting mixture was stirred for about 30 minutes, and dilute hydrochloric acid was dropwise added to the mixture to adjust the mixture to pH 2 or less.

The above-mentioned mixture was separated into two layers on standing. The organic layer was washed with water until a reaction product crystallized. As a result, 131.3 g of white crystals was obtained in a 78% yield. This reaction product was a composition made of three kinds of isomers. The purity of the composition was 87.2% when measured by gel permeation chromatography (GPC). Although the melting point of the product was ambiguous, the corresponding reaction product was identified as the expected composition by the analysis of $^1$H-NMR.

δ (ppm)=13.53 (broad s), 8.20 (4H, t), 7.77 (2H, t), 7.77 (4H, d), 7.12 (4H, d), 6.86 (4H, d), 454 (4H, broad s), 4.24 (4H, broad s), 1.56 (6H, s).

PREPARATION EXAMPLE 4

[Synthesis of composition No. 53 or aromatic carboxylic acid compounds employing a bivalent group X represented by No. 53 in Table 1]

A mixture of 34.5 g (0.25 mol) of 1,4-bis(hydroxymethyl) benzene, 114.1 g (0.60 mol) of trimellitic acid anhydride, and 151.5 g (1.50 mol) of triethylamine was suspended in a mixed solvent of 150 g of tetrahydrofuran and 50 g of dimethylformamide in a reaction vessel. The mixture was heated at about 83° C. under reflux to carry out the reaction for 3 hours.

After the reaction mixture was cooled, 100 ml of water was dropwise added to the reaction mixture. The resulting mixture was stirred for about 30 minutes, and dilute hydrochloric acid was dropwise added to the mixture to adjust the mixture to pH 2 or less.

The above-mentioned mixture was separated into two layers on standing. The organic layer was washed with water until a reaction product crystallized. As a result, 125.8 g of white crystals was obtained in a 96% yield. This reaction product was a composition made of three kinds of isomers. The purity of the composition was 94.2% (when measured by the HPLC), and there were observed the melting points thereof at 191° C. and 249° C. The corresponding reaction product was identified as the expected composition by the analysis of $^1$H-NMR.

δ (ppm)=8.21 (4H, t), 7.81 (2H, t), 7.48 (4H, s), 5.33 (4H, s).

PREPARATION EXAMPLE 5

[Synthesis of composition No. 56 of aromatic carboxylic acid compounds employing a bivalent group X represented by No. 56 in Table 1]

A mixture of 49.6 g (0.25 mol) of 1,4-bis(2-hydroxyethoxy)benzene, 114.1 g (0.60 mol) of trimellitic acid anhydride, and 151.5 g (1.50 mol) of triethylamine was suspended in a mixed solvent of 150 g of tetrahydrofuran and 50 g of dimethylformamide in a reaction vessel. The mixture was heated at about 83° C. under reflux to carry out the reaction for 3 hours.

After the reaction mixture was cooled, 100 ml of water was dropwise added to the reaction mixture. The resulting mixture was stirred for about 30 minutes, and dilute hydrochloric acid was dropwise added to the mixture to adjust the mixture to pH 2 or less.

The above-mentioned mixture was separated into two layers on standing. The organic layer was washed with water until a reaction product crystallized. As a result, 144.0 g of pale yellow-white crystals was obtained in a 99% yield. This reaction product was a composition made of three kinds of isomers. The purity of the composition was 92.2% (when measured by the HPLC), and the melting point thereof was 218° C. The corresponding reaction product was identified as the expected composition by the analysis of $^1$H-NMR.

δ (ppm)=13.58 (broad s), 8.20 (4H, t), 7.85 (2H, t), 6.91 (4H, s), 4.54 (4H, broad s), 4.25 (4H, broad s).

PREPARATION EXAMPLE 6

[Synthesis of composition No. 16 of aromatic carboxylic acid compounds employing a bivalent group X represented by No. 16 in Table 1]

A mixture of 30.5 g (0.25 mol) of bis(2-hydroxyethyl) sulfide, 114.1 g (0.60 mol) of trimellitic acid anhydride, and 151.5 g (1.50 mol) of triethylamine was suspended in a mixed solvent of 150 g of tetrahydrofuran and 50 g of dimethylformamide in a reaction vessel. The mixture was heated at about 83° C. under reflux to carry out the reaction for 3 hours.

After the reaction mixture was cooled, 100 ml of water was dropwise added to the reaction mixture. The resulting mixture was stirred for about 30 minutes, and dilute hydrochloric acid was dropwise added to the mixture to adjust the mixture to pH 2 or less.

The above-mentioned mixture was separated into two layers on standing. The organic layer was washed with water until a reaction product crystallized. As a result, 96.1 g of pale yellow-brown crystals was obtained in a 76% yield. This reaction product was a composition made of three kinds of isomers. The purity of the composition was 95.0% (when measured by the HPLC), and the melting point thereof was 166° C. The corresponding reaction product was identified as the expected composition by the analysis of $^1$H-NMR.

δ (ppm)=13.46 (broad s), 8.21 (4H, t), 7.78 (2H, t), 4.42 (4H, t), 2.93 (4H, t).

PREPARATION EXAMPLE 7

[Synthesis of composition No. 3 of aromatic carboxylic acid compounds employing a bivalent group X represented by No. 3 in Table 1]

A mixture of 22.5 g (0.25 mol) of 1,4-butanediol, 114.1 g (0.60 mol) of trimellitic acid anhydride, and 151.5 g (1.50 mol) of triethylamine was suspended in a mixed solvent of 150 g of tetrahydrofuran and 50 g of dimethylformamide in a reaction vessel. The mixture was heated at about 83° C. under reflux to carry out the reaction for 3 hours.

After the reaction mixture was cooled, 100 ml of water was dropwise added to the reaction mixture. The resulting mixture was stirred for about 30 minutes, and dilute hydrochloric acid was dropwise added to the mixture to adjust the mixture to pH 2 or less.

The above-mentioned mixture was separated into two layers on standing. The organic layer was washed with water until a reaction product crystallized. As a result, 109.8 g of pale yellow-white crystals was obtained in a 93% yield. This reaction product was a composition made of three kinds of isomers. The purity of the composition was 97.3% (when measured by HPLC), and there were observed the melting points thereof at 99° C., 183° C., and 242–258° C. The corresponding reaction product was identified as the expected composition by the analysis of $^1$H-NMR.

δ (ppm)=13.45 (broad s), 8.25 (2H, d), 8.15 (2H, m), 7.79 (2H, t), 4.31 (4H, broad s), 1.81 (4H, broad s).

PREPARATION EXAMPLE 8
[Synthesis of composition No. 7 of aromatic carboxylic acid compounds employing a bivalent group X represented by No. 7 in Table 1]

A mixture of 43.6 g (0.25 mol) of 1,10-decanediol, 114.1 (0.60 mol) of trimellitic acid anhydride, and 151.5 g (1.50 mol) of triethylamine was suspended in a mixed solvent of 150 g of tetrahydrofuran and 50 g of dimethylformamide in a reaction vessel. The mixture was heated at about 83° C. under reflux to carry out the reaction for 3 hours.

After the reaction mixture was cooled, 100 ml of water was dropwise added to the reaction mixture. The resulting mixture was stirred for about 30 minutes, and dilute hydrochloric acid was dropwise added to the mixture to adjust the mixture to pH 2 or less.

The above-mentioned mixture was separated into two layers on standing. The organic layer was washed with water until a reaction product crystallized. As a result, 131.4 g of white crystals was obtained in a 94% yield. This reaction product was a composition made of three kinds of isomers. The purity of the composition was 97.1% (when measured by the HPLC), and there were observed the melting points thereof at 160° C., 185° C., and 226° C. The corresponding reaction product was identified as the expected composition by the analysis of $^1$H-NMR.

δ (ppm)=13.48 (broad s), 8.19 (4H, m), 7.77 (2H, t), 4.23 (4H, t), 1.63 (4H, broad s), 1.28 (12H, s).

PREPARATION EXAMPLE 9
[Synthesis of composition No. 10 of aromatic carboxylic acid compounds employing a bivalent group X represented by No. 10 in Table 1]

A mixture of 37.5 g (0.25 mol) of tri(ethylene glycol), 114.1 g (0.60 mol) of trimellitic acid anhydride, and 151.5 g (1.50 mol) of triethylamine was suspended in a mixed solvent of 150 g of tetrahydrofuran and 50 g of dimethylformamide in a reaction vessel. The mixture was heated at about 83° C. under reflux to carry out the reaction for 3 hours.

After the reaction mixture was cooled, 100 ml of water was dropwise added to the reaction mixture. The resulting mixture was stirred for about 30 minutes, and dilute hydrochloric acid was dropwise added to the mixture to adjust the mixture to pH 2 or less.

The above-mentioned mixture was separated into two layers on standing. The organic layer was washed with water until a reaction product crystallized. As a result, 66.8 g of pale yellow crystals was obtained in a 50% yield. This reaction product was a composition made of three kinds of isomers. The purity of the composition was 90.8% (when measured by the HPLC), and there were observed the melting points thereof at 163° C., and 214–234° C. The corresponding reaction product was identified as the expected composition by the analysis of $^1$H-NMR.

δ (ppm)=13.53 (broad s), 8.17 (4H, t), 7.77 (2H, t), 4.37 (4H, t), 3.71 (4H, t), 3.58 (4H, s).

EXAMPLE 1
[Preparation of thermosensitive recording material No. 1]

A mixture of the following components was separately dispersed in a procelain ball mill, so that a Liquid A, a Liquid B, a Liquid C, and a Liquid D were prepared:

|  | Parts by Weight |
| --- | --- |
| [Liquid A] | |
| 3-N,N-dibutylamino-6-methyl-7-anilinofluoran | 10 |
| 10% aqueous solution of poly(vinyl alcohol) | 10 |
| [Liquid B] | |
| Composition No. 38 (prepared in Preparation Example 1) | 10 |
| 10% aqueous solution of poly(vinyl alcohol) | 10 |
| Water | 30 |
| [Liquid C] | |
| Silica gel (Trademark "P527" made by Mizusawa Industrial Chemicals, Ltd.) | 10 |
| 10% aqueous solution of poly(vinyl alcohol) | 10 |
| Water | 30 |
| [Liquid D] | |
| Zinc stearate | 10 |
| 10% aqueous solution of poly(vinyl alcohol) | 10 |
| Water | 30 |

A mixture of the following components was stirred and dispersed in a dispersion mixer, so that a Liquid E was prepared:

| [Liquid E] | |
| --- | --- |
|  | Parts by Weight |
| Unexpanded minute void plastic particles (solid content: 24 wt. %, average particle diameter: 3 μm, and voidage: 90%) | 40 |
| Styrene - butadiene copolymer latex | 10 |
| Water | 50 |

[Formation of undercoat layer]

The Liquid E and the Liquid C were mixed at a ratio by weight of 2:1, so that a coating liquid for an undercoat layer was prepared. The thus prepared undercoat layer coating liquid was coated on a sheet of commercially available high quality paper with a basis weight of 60 g/m$^2$, serving as a support, and then dried so as to have a deposition amount of 3 g/m$^2$ on a dry basis, whereby an undercoat layer was formed on the support.

[Formation of thermosensitive coloring layer]

The Liquid A, the Liquid B, the Liquid C, and the Liquid D were mixed at a ratio by weight of 1:4:4:0.5 to prepare a thermosensitive coloring layer coating liquid. The thus prepared thermosensitive coloring layer coating liquid was coated on the above prepared undercoat layer and then dried so that the deposition amount of the leuco dye was 0.5 g/m$^2$ on a dry basis, whereby a thermosensitive coloring layer was formed on the undercoat layer.

The surface of the thermosensitive coloring layer thus obtained was subjected to calendering with the application of a pressure of 10 kg/cm².

Thus, a thermosensitive recording material No. 1 according to the present invention was obtained.

EXAMPLE 2

The procedure for preparation of the thermosensitive recording material No. 1 in Example 1 was repeated except that the Composition No. 38 in the Liquid B for the thermosensitive coloring layer coating liquid in Example 1 was replaced by Composition No. 40 prepared in Preparation Example 2.

Thus, a thermosensitive recording material No. 2 according to the present invention was obtained.

EXAMPLE 3

The procedure for preparation of the thermosensitive recording material No. 1 in Example 1 was repeated except that the Composition No. 38 in the Liquid B for the thermosensitive coloring layer coating liquid in Example 1 was replaced by Composition No. 32 prepared in Preparation Example 3.

Thus, a thermosensitive recording material No. 3 according to the present invention was obtained.

EXAMPLE 4

The procedure for preparation of the thermosensitive recording material No. 1 in Example 1 was repeated except that the Composition No. 38 in the Liquid B for the thermosensitive coloring layer coating liquid in Example 1 was replaced by composition No. 53 prepared in Preparation Example 4.

Thus, a thermosensitive recording material No. 4 according to the present invention was obtained.

EXAMPLE 5

The procedure for preparation of the thermosensitive recording material No. 1 in Example 1 was repeated except that the Composition No. 38 in the liquid B for the thermosensitive coloring layer coating liquid in Example 1 was replaced by Composition No. 56 prepared in Preparation Example 5.

Thus, a thermosensitive recording material No. 5 according to the present invention was obtained.

EXAMPLE 6

The procedure for preparation of the thermosensitive recording material No. 1 in Example 1 was repeated except that the Composition No. 38 in the Liquid B for the thermosensitive coloring layer coating liquid in Example 1 was replaced by Composition No. 16 prepared in Preparation Example 6.

Thus, a thermosensitive recording material No. 6 according to the present invention was obtained.

EXAMPLE 7

The procedure for preparation of the thermosensitive recording material No. 1 in Example 1 was repeated except that the Composition No. 38 in the Liquid B for the thermosensitive coloring layer coating liquid in Example 1 was replaced by Composition No. 3 prepared in Preparation Example 7.

Thus, a thermosensitive recording material No. 7 according to the present invention was obtained.

EXAMPLE 8

The procedure for preparation of the thermosensitive recording material No. 1 in Example 1 was repeated except that the Composition No. 38 in the Liquid B for the thermosensitive coloring layer coating liquid in Example 1 was replaced by Composition No. 7 prepared in Preparation Example 8.

Thus, a thermosensitive recording material No. 8 according to the present invention was obtained.

EXAMPLE 9

The procedure for preparation of the thermosensitive recording material No. 1 in Example 1 was repeated except that the Composition No. 38 in the Liquid B for the thermosensitive coloring layer coating liquid in Example 1 was replaced by composition No. 10 prepared in Preparation Example 9.

Thus, a thermosensitive recording material No. 9 according to the present invention was obtained.

COMPARISON EXAMPLE 1

The procedure for preparation of the thermosensitive recording material No. 1 in Example 1 was repeated except that the Composition No. 38 in the Liquid B for the thermosensitive coloring layer coating liquid in Example 1 was replaced by 2,2-bis(4-hydroxyphenyl)propane, that is bisphenol A.

Thus, a comparative thermosensitive recording material No. 1 was obtained.

(Measurement of Coloring Density of Image)

Each of the thermosensitive recording materials Nos. 1 to 9 according to the present invention obtained in Examples 1 to 9 and the comparative thermosensitive recording material No. 1 obtained in Comparative Example 1 was loaded in a printing test apparatus equipped with a commercially available thin film head (made by Matsushita Electronic Components Co., Ltd.), and images were formed on each recording material under the conditions that the applied electric power was 0.68 W/dot, the period for one line was 10 ms/line, the scanning line density was 8×3.85 dot/mm, and the pulse width was 0.9 msec. Thus, image samples were prepared.

The coloring density of the image recorded on each image sample was measured by a McBeth densitometer.

The results are shown in TABLE 2.

(Evaluation of Preservation Stability of Recorded Image)

1. Plasticizer resistance test

Three sheets of commercially available vinyl chloride wrap, made by Shin-Etsu Polymer Co., Ltd., were overlaid on the above prepared image sample. Each sample was allowed to stand at 40° C. with the application of a load of 5 kg thereto for 15 hours.

After 15 hours, the coloring density of the image was measured using the McBeth densitometer to evaluate the plasticizer resistance.

The results are also shown in TABLE 2.

2. Oil resistance test

After cottonseed oil was applied to each image sample, the image sample was allowed to stand at 40° C. for 15 hours.

After 15 hours, the coloring density of the image was measured using the McBeth densitometer to evaluate the oil resistance.

The results are also shown in TABLE 2.

TABLE 2

|  | Coloring Density at Initial Stage | Coloring Density after Plasticizer Resistance Test | Coloring Density after Oil Resistance Test |
| --- | --- | --- | --- |
| Ex. 1 | 1.16 | 1.19 | 1.27 |
| Ex. 2 | 1.04 | 0.92 | 1.03 |
| Ex. 3 | 1.27 | 1.16 | 1.35 |
| Ex. 4 | 1.07 | 0.84 | 1.14 |
| Ex. 5 | 1.18 | 0.90 | 1.23 |
| Ex. 6 | 1.26 | 1.23 | 1.32 |
| Ex. 7 | 1.26 | 1.21 | 1.31 |
| Ex. 8 | 0.87 | 0.70 | 0.98 |
| Ex. 9 | 0.98 | 0.93 | 1.13 |
| Comp. Ex. 1 | 1.42 | 0.19 | 0.45 |

As is apparent from the results shown in TABLE 2, when the composition of the aromatic carboxylic acid compounds represented by the formulas (I) to (III) according to the present invention is used as the color developer in the thermosensitive recording material, the colored images formed in the recording material exhibit excellent preservation stability, in particular, with respect to the plasticizer resistance and the oil resistance.

Japanese Patent Application No. 11-109772 filed Apr. 16, 1999 and Japanese Patent Application No. 11-109773 filed Apr. 16, 1999 are hereby incorporated by reference.

What is claimed is:

1. A composition comprising at least two aromatic carboxylic acid compounds selected from the group consisting of aromatic carboxylic acid compounds of formulas (I), (II) and (III):

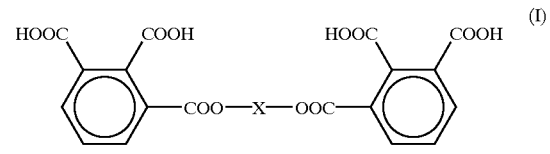

(I)

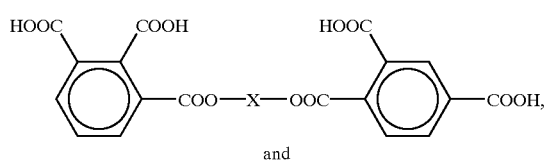

(II)

and

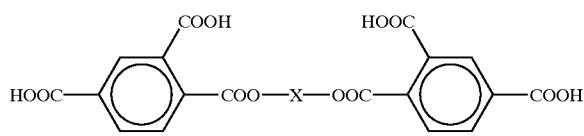

(III)

wherein X represents carbonyl group; sulfonyl group; a bivalent group derived from an aliphatic hydrocarbon; a bivalent group derived from an aliphatic hydrocarbon comprising in the main chain thereof at least one hetero atom, carbonyl group, sulfonyl group, an ester linkage, or an aromatic ring; or a bivalent group derived from an aromatic hydrocarbon compound prepared by connecting two aromatic hydrocarbons via at least one hetero atom, carbonyl group, sulfonyl group, an ester linkage, an alkylene, or an aliphatic hydrocarbon comprising a hetero atom in the main chain thereof.

2. The composition as claimed in claim 1, wherein said bivalent functional group of X in formulas (I) to (III) is represented by formula (IV):

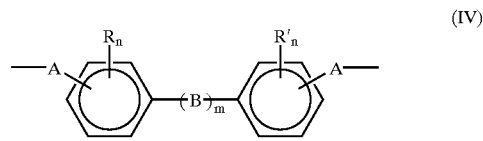

(IV)

wherein R and R' which may be the same or different are each a hydrogen atom, a halogen atom, an alkyl group having 1 to 8 carbon atoms, an aralkyl group having 1 to 8 carbon atoms, or an aryl group having 1 to 8 carbon atoms; n is an integer of 1 to 4; m is an integer of 0 or 1; and A and B are each carbonyl group, sulfonyl group, a bivalent group derived from an aliphatic hydrocarbon, a bivalent group derived from an aliphatic hydrocarbon comprising in the main chain thereof at least one hetero atom, carbonyl group, sulfonyl group, an ester linkage, or an aromatic ring, or a bivalent group derived from an aromatic hydrocarbon compound prepared by connecting two aromatic hydrocarbons via at least one hetero atom, carbonyl group, sulfonyl group, an ester linkage, an alkylene, or an aliphatic hydrocarbon comprising a hetero atom in the main chain thereof.

3. The composition as claimed in claim 2, wherein said bivalent functional group represented by B in formula (IV) is sulfonyl group.

4. The composition as claimed in claim 1, wherein said bivalent functional group represented by X in formulas (I) to (III) is derived from a bivalent group selected from the group consisting of an alkylene, oxyalkylene, thioalkylene, sulfinylalkylene, and sulfonylalkylene, each having 1 to 16 carbon atoms.

5. A thermosensitive recording material comprising a support and a thermosensitive coloring layer formed thereon comprising a leuco dye and a color developer capable of inducing color formation in said leuco dye upon application of heat thereto, with said color developer comprising a composition comprising at least two aromatic carboxylic acid compounds selected from the group consisting of aromatic carboxylic acid compounds of formulas (I), (II) and (III):

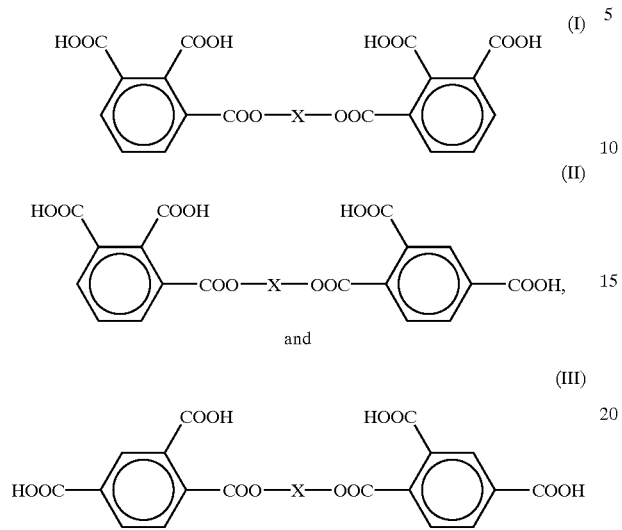

wherein X represents carbonyl group; sulfonyl group; a bivalent group derived from an aliphatic hydrocarbon; a bivalent group derived from an aliphatic hydrocarbon comprising in the main chain thereof at least one hetero atom, carbonyl group, sulfonyl group, an ester linkage, or an aromatic ring; or a bivalent group derived from an aromatic hydrocarbon compound prepared by connecting two aromatic hydrocarbons via at least one hetero atom, carbonyl group, sulfonyl group, an ester linkage, an alkylene, or an aliphatic hydrocarbon comprising a hetero atom in the main chain hereof.

6. The thermosensitive recording material as claimed in claim 5, wherein said bivalent functional group of X in formulas (I) to (III) is represented by formula (IV):

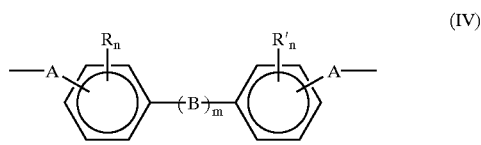

wherein R and R' which may be the same or different are each a hydrogen atom, a halogen atom, an alkyl group having 1 to 8 carbon atoms, an aralkyl group having 1 to 8 carbon atoms, or an aryl group having 1 to 8 carbon atoms; n is an integer of 1 to 4; m is an integer of 0 or 1; and A and B are each carbonyl group, sulfonyl group, a bivalent group derived from an aliphatic hydrocarbon, a bivalent group derived from an aliphatic hydrocarbon comprising in the main chain thereof at least one hetero atom, carbonyl group, sulfonyl group, an ester linkage, or an aromatic ring, or a bivalent group derived from an aromatic hydrocarbon compound prepared by connecting two aromatic hydrocarbons via at least one hetero atom, carbonyl group, sulfonyl group, an ester linkage, an alkylene, or an aliphatic hydrocarbon comprising a hetero atom in the main chain thereof.

7. The thermosensitive recording material as claimed in claim 6, wherein said bivalent functional group represented by B in formula (IV) is sulfonyl group.

8. The thermosensitive recording material as claimed in claim 5, wherein said bivalent functional group represented by X in formulas (I) to (III) is derived from a bivalent group selected from the group consisting of an alkylene, oxyalkylene, thioalkylene, sulfinylalkylene, and sulfonylalkylene, each having 1 to 16 carbon atoms.

* * * * *